(12) United States Patent
Koehler

(10) Patent No.: US 8,627,824 B2
(45) Date of Patent: Jan. 14, 2014

(54) SUPPORT ASSEMBLY FOR AN EAR

(76) Inventor: Robert Grant Koehler, Mahtomedi, MN (US)

( * ) Notice: Subject to any disclaimer, the term of this patent is extended or adjusted under 35 U.S.C. 154(b) by 0 days.

(21) Appl. No.: 13/213,311

(22) Filed: Aug. 19, 2011

(65) Prior Publication Data

US 2012/0179078 A1    Jul. 12, 2012

Related U.S. Application Data

(63) Continuation of application No. PCT/US2010/025204, filed on Feb. 24, 2010.

(60) Provisional application No. 61/154,971, filed on Feb. 24, 2009, provisional application No. 61/177,419, filed on May 12, 2009.

(51) Int. Cl.
*A61F 9/00* (2006.01)

(52) U.S. Cl.
USPC .............................. 128/858; 602/2

(58) Field of Classification Search
USPC ...................... 602/2; 128/846, 857, 864, 866; 181/126, 128, 129, 130, 135; 381/328, 381/380; 2/9, 171.2, 209, 423, 425; 607/109, 112; 606/201, 204, 204.15
See application file for complete search history.

(56) References Cited

U.S. PATENT DOCUMENTS

| 520,785 | A | * | 6/1894 | Jung | 2/209 |
|---|---|---|---|---|---|
| 1,066,511 | A | * | 7/1913 | Markoff | 128/866 |
| 1,700,844 | A | | 2/1929 | Hess | |
| 1,824,835 | A | | 9/1931 | Pierce | |
| 2,473,723 | A | | 6/1949 | Nelson | |
| 3,257,668 | A | | 6/1966 | Braley | |
| 3,475,528 | A | | 10/1969 | Parks | |
| 3,513,269 | A | | 5/1970 | Wilson | |
| 3,588,914 | A | * | 6/1971 | Ihnat, Jr | 2/421 |
| 3,823,713 | A | | 7/1974 | Shah | |
| 3,833,701 | A | | 9/1974 | Johnson | |
| 3,889,684 | A | * | 6/1975 | Lebold | 607/109 |
| 4,037,273 | A | | 7/1977 | LaBaire | |
| 4,187,838 | A | | 2/1980 | Dubrowski | |
| 4,335,067 | A | | 6/1982 | Castanis et al. | |
| 4,670,911 | A | * | 6/1987 | Dunford | 2/209 |
| 4,672,081 | A | * | 6/1987 | Fisher et al. | 523/109 |
| 4,713,843 | A | * | 12/1987 | Duncan | 2/209 |

(Continued)

FOREIGN PATENT DOCUMENTS

WO    WO 2005025465    3/2005

OTHER PUBLICATIONS

Thomas M. Keating, MD and John Mason, ATC, A Simple Splint for Wrestler's Ear, 1992, vol. 27, No. 3, pp. 1-2.

(Continued)

*Primary Examiner* — Patricia Bianco
*Assistant Examiner* — Raymond E Harris
(74) *Attorney, Agent, or Firm* — Steven M. Koehler; Westman, Champlin & Koehler, P.A.

(57) ABSTRACT

An ear support assembly and a method for applying pressure to an ear includes a support device having solid planar or curved surfaces and formable material configured to be deformed and retain an impression of a surface of an ear, wherein the planar or curved surfaces are configured to apply pressure to the formable material such that the formable material applies pressure to the surface of the ear.

20 Claims, 13 Drawing Sheets

(56) References Cited

U.S. PATENT DOCUMENTS

| | | | |
|---|---|---|---|
| 4,834,927 A | 5/1989 | Birkholz et al. | |
| 4,872,219 A * | 10/1989 | Duncan | 2/209 |
| 5,295,950 A * | 3/1994 | Godley | 602/53 |
| 5,433,748 A | 7/1995 | Wellisz | |
| 5,551,090 A * | 9/1996 | Thompson | 2/209 |
| 5,615,417 A * | 4/1997 | Jackson | 2/209 |
| 5,673,438 A * | 10/1997 | Lambert | 2/209 |
| 5,827,212 A | 10/1998 | Gaskill | |
| 6,093,202 A * | 7/2000 | Dyken et al. | 607/109 |
| 6,195,806 B1 * | 3/2001 | Campbell | 2/209 |
| 6,402,782 B1 | 6/2002 | Sibbald et al. | |
| 6,517,557 B1 | 2/2003 | Sorribes | |
| 6,986,167 B1 * | 1/2006 | Coutant et al. | 2/425 |
| 7,093,600 B2 | 8/2006 | Sorribes | |
| 7,117,546 B2 * | 10/2006 | Goulding | 2/423 |
| 7,153,313 B2 | 12/2006 | Whitton | |
| 7,335,222 B1 * | 2/2008 | Tyler | 607/109 |
| 7,469,429 B1 * | 12/2008 | Lanclos | 2/209 |
| 7,799,075 B2 | 9/2010 | Kang et al. | |
| 8,136,530 B2 * | 3/2012 | Byrd et al. | 128/864 |
| 2006/0161184 A1 | 7/2006 | Whitton | |
| 2008/0086067 A1 | 4/2008 | Hay et al. | |
| 2008/0119774 A1 | 5/2008 | Paasche | |
| 2009/0182255 A1 | 7/2009 | Hay | |

OTHER PUBLICATIONS

International Search Report from the Korean Intellectual Property Office for corresponding foreign application PCT/US2010/025204, Jul. 2009.

* cited by examiner

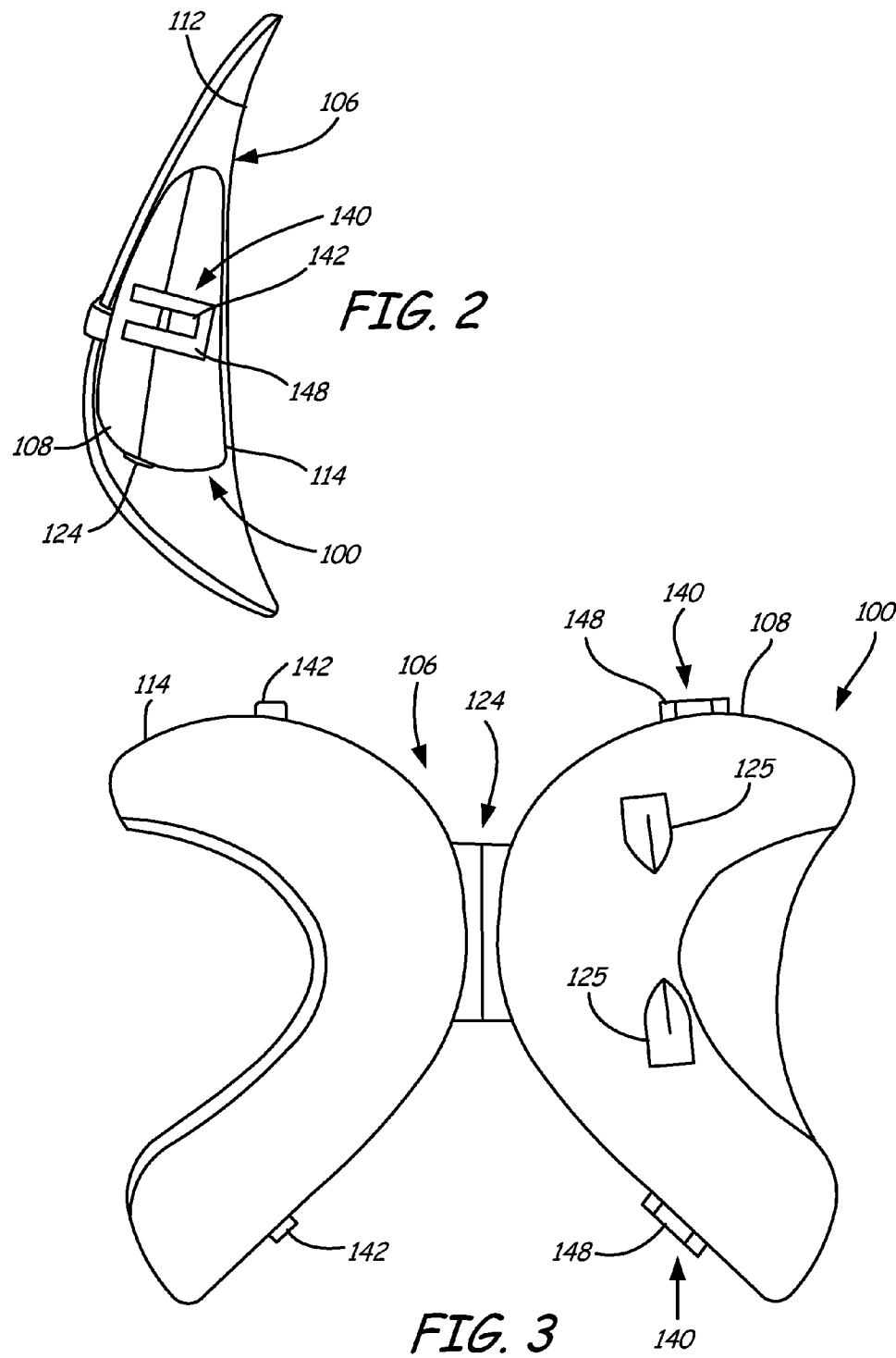

SUPPORT ASSEMBLY FOR AN EAR

CROSS REFERENCE TO RELATED APPLICATION

The present application is a continuation of and claims priority of International patent application Serial No. PCT/US2010/025204, filed Feb. 24, 2010, and published in English, which claims the benefit of U.S. Provisional Patent applications entitled "SUPPORT ASSEMBLY FOR AN EAR," having Ser. No. 61/154,971, filed Feb. 24, 2009, and "SUPPORT ASSEMBLY FOR AN EAR," having Ser. No. 61/177,419, filed May 12, 2009, all of which are incorporated herein by reference in their entirety.

BACKGROUND

The discussion below is merely provided for general background information and is not intended to be used as an aid in determining the scope of the claimed subject matter.

Cauliflower ear, also known as hematoma auris, perichondrial hematoma, and traumatic auricular hematoma, occurs when the ear suffers physical damage from, for example, a blow, rubbing of the ear with high pressure, or the like. This form of trauma to the ear is most common among boxers, wrestlers, rugby players, and mixed martial arts players. Damage occurs because the cartilage separates from the overlying perichondrium and fluid such as blood collects under the perichondrium. Untreated, this leads to a formation of fibrous tissue in the overlying skin. In such cases, the outer ear becomes permanently swollen and deformed, resembling a cauliflower.

Many sporting contests encourage the use of headgear in order to minimize trauma to the ear. However, damage can occur if the headgear is improperly worn. Moreover though, some participants choose not to wear such headgear.

As indicated above, the ear can become permanently swollen, if untreated. Some forms of treatment to prevent cauliflower ear include draining the fluid from the ear when trauma has ocurred and applying a compressing tie or wrap around the patient's head in conjunction with an impression made previously of the ear with a formable material. The compressing tie or wrap is used to apply pressure to the formable material and ear in order to reduce swelling or pooling of fluid. It is desirable to leaving the compression tie or wrap on for multiple days such as 5-9 days. During that time however, it is occasionally necessary to remove the tie or wrap in order to take a shower, clean or otherwise examine the ear. The impression(s) and the tie or wrap then need to be reapplied, which can be cumbersome. Overall, the process and equipment makes compliance for the desired term troublesome.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

A first aspect of the present invention is an ear support assembly including a support device having solid planar or curved surfaces and formable material configured to be deformed and retain an impression of a surface of an ear, wherein the planar or curved surfaces are configured to apply pressure to the formable material such that the formable material applies pressure to the surface of the ear.

A second aspect of the present invention is a method of applying pressure to a surface of an ear, the method includes: providing a support device having solid planar or curved surfaces; disposing formable material between the support device and a surface of the ear; and applying pressure to the support device so as to apply pressure through the formable material and thereby to the surface of the ear. In these aspects, the support device can be a rigid or semi-rigid body made from material such as but not limited to plastic, rubber, polymers, metal, or the like, or combinations thereof.

The features described below can be optionally included alone or in combination as desired with each of the foregoing aspects.

The support device can include a first portion of size to be disposed between the ear and a skull of the user, and a second portion of size to be disposed so as to cover a surface of the ear facing away from the skull of the user. The formable material is disposed so as to contact a surface of the ear facing the skull of the user and a surface of the ear facing away from the skull of the user. Each portion of the support device is configured to apply pressure to each of the formable materials such that each of the formable materials applies pressure to the corresponding surface of the ear. The first portion and the second portion can be selectively engagable with each other using one of a hinge or a bendable section that joins the first and second portions together, although use of a hinge or bendable portion is not required in that the first and second portion can comprise separate elements having complementary surfaces that engage each other and retain or hold them together as a single unit.

A fastener can be provided to releasably secure the portions together. The fastener can take numerous forms such as but not limited to latches, clips, catches, snaps and hook and loop fasteners. The fastener can be configured to hold the portions together at selected varying distances from each other, which can allow varying amounts of pressure to be applied to the ear surfaces and/or adjust the position of the formable material so as to continue to apply pressure as swelling and/or pooling diminishes. If desired, a removable stop can be provided on one or both of the portions so as to limit the distance that the portions can be brought together, for example, during the step of applying pressure to the formable material to obtain impression(s) of the ear surfaces. After removal of the stop, the portions can then be brought closer together for the reasons discussed above.

In one embodiment, the first portion and the second portion can form an enclosure for enclosing at least a portion of the ear. If desired, the second portion, the first portion and/or the enclosure can be crescent shaped so as to conform to the ear.

The ear support assembly can include a restraint such as but not limited to a strap or flexible arm that is configured to be worn on the head of the user and apply the pressure to the formable material, wherein the restraint is fixedly coupled or releasably coupled to the support device or portion(s).

If desired, the support device or portion(s) can include an attachment structure such as but not limited to upstanding projections, recesses, apertures, ribs or the like for retaining the formable material on the support device or portions.

In one embodiment, an insert can be provided where the insert includes a recess or other structure configured to receive the ear support assembly, wherein the insert is further configured to be disposed in protective headgear.

Insert(s) comprising refrigerant material can also be included in the ear support assembly. In one embodiment, the insert(s) engages at least some of the formable material to keep the formable material cool for a period of time. The insert(s) can be attached to or molded with the support device. The inserts(s) can also be imbedded in the formable material.

In one embodiment, the support device or portions can include one or more venting apertures.

BRIEF DESCRIPTION OF THE DRAWINGS

FIG. 2 is a top plan view of the ear support assembly and the portion of the holding strap.

FIG. 3 is an elevational view of outer surfaces of a support device for the ear support assembly in an open position.

DETAILED DESCRIPTION OF ILLUSTRATIVE EMBODIMENTS

Various embodiments of ear support assemblies are discussed below and illustrated in the Figures. Generally, the ear support assembly includes a rigid or semi-rigid support device to hold formable material against at least a portion of the ear in order to make an impression thereof. The support device includes planar or curved solid surfaces that engage the formable material to apply pressure for making an impression of the ear. After the impression(s) has been made, the support device and formable material can then be easily repositioned back on the user's ear when injury has possibly occurred in order to reduce swelling and/or pooling of fluid such as blood. Rather than using a tie or wrap to retain the impressions against the ear, the formable material is directly, fixedly attached or otherwise retained by the support device, which allows the impression(s) to be positioned easily back on the ear so that the impression(s) can properly engage the ear.

Figure 8:
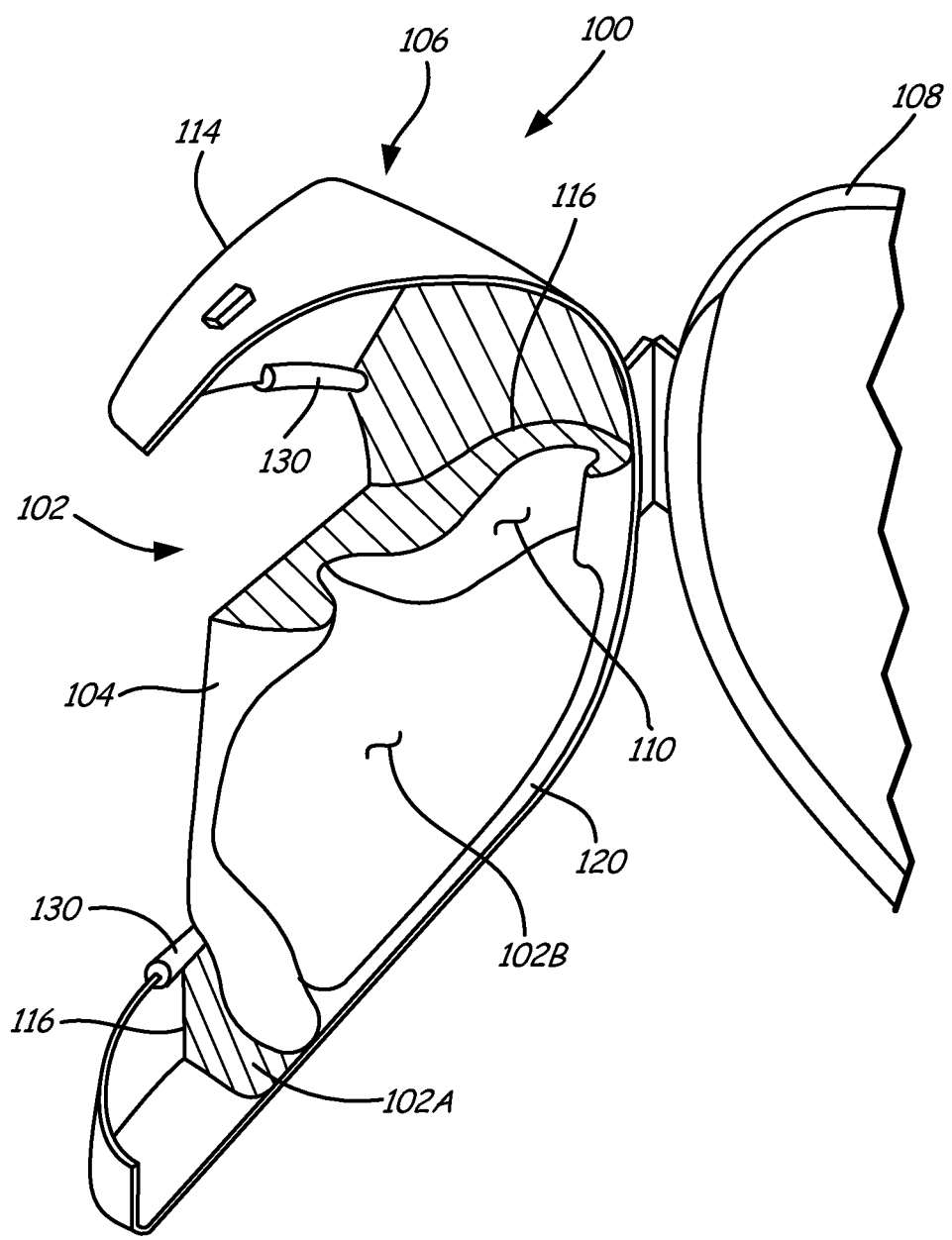
FIG. 8 is a partial perspective view of an ear support assembly with an ear and front and back portions of formable material shown in section.

A first embodiment of an ear support assembly 100 is illustrated in FIGS. 1-5 and 8. Referring to FIG. 8, the ear support assembly 100 generally includes formable material 102 that is configured to conform to selected surfaces of an ear 104. In this embodiment, the support device comprises a housing 106 having inner planar and curved surfaces that hold the formable material 102 in position and against the ear 104 with pressure so as to inhibit swelling and/or pooling of fluid such as blood which can occur after a trauma.

In the embodiment illustrated, the housing 106 includes a first portion 108 that is disposed over surfaces 110 of the ear 104 facing away from a user's skull 112 to hold or retain formable material against surfaces 110, while a second portion 114 of the housing 106 is disposed over surfaces 116 of the user's ear 104 that generally face the user's skull 112. The second portion 114 of the housing 106 holds or retains formable material against surfaces 116. Generally, each portion 108, 114 of the housing 106 assists the user in making an impression of the user's ear 104 as well as supports the formable material 102 against the ear 104 once the impressions have been made in order to support the folds and other portions of the ear to prevent hematomas or other problems of the like from occurring.

Application of the ear support assembly 100 can be performed as follows, although the order of the steps can be altered or different, if desired. The second portion 114 of the housing 106 is disposed behind the user's ear 104 and generally held in a stationary position, for example, by being pressed against the user's skull 112. As illustrated in FIG. 8, the formable material 102 is then positioned behind the user's ear 104 in a manner so as to contact surfaces 116 of the user's ear 104 and inner surfaces of housing portion 114, while taking care that the ear 104 stays in a natural position.

Generally, the formable material 102 is disposed so as to engage surfaces 110 and/or 116 of the ear 104 in order to obtain a natural impression thereof. The formable material 102 can be one continuous portion so as to obtain impressions of surfaces 110 and 112, and thus also some or all of an outer rim or edge 120 of the ear 104 including a helix (not shown). Alternatively, the formable matter 102 can also be separated into two or more portions as desired in order to obtain desired impressions of the ear. Whether as a portion from the formable material placed behind the ear 104, or as a separate portion, formable material 102 is also placed on the surface 110 of the ear, whereupon the first portion of the 108 and inner surfaces thereof engage the formable material 102 to make a corresponding impression. If desired, an element such as a rod (not shown) can be positioned with one end proximate the ear canal and the formable material 102 is positioned around the rod. In this manner, an opening is provided in the formable material 102 leading to the ear canal, which can improve hearing when the ear support assembly 100 is worn.

After the formable material 102 has been suitably deformed to the surface(s) of the ear 104, the formable material 102 is then allowed to dry, cure or otherwise set up. Typically, drying or curing occurs while pressure is exerted upon, or maintained by, the portions 108 and 114. After drying, curing or otherwise setting up, the formable material 102 achieves at least a less malleable state where impressions of the surfaces of the ear are made therein and the resulting impressions can be used at a later time to apply pressure to the ear 104 and reduce swelling and/or pooling of fluid.

One formable material that can be used is "Friendly Plastic". Friendly plastic is a pliable putty type clear plastic. Friendly Plastic is a product of the American Art Clay Company of Indianapolis, Ind. Other types of formable material are "President Putty" or "Affinis Putty", products of Coltene Whaledent of Cuyahoga Falls, Ohio; putty from Crown Delta of Yorktown Heights, N.Y.; 3M ESPE Impression Material from 3M of St. Paul, Minn.; "EXA'lence Putty" from GC America Inc. of Alsip, Ill. and "Dur-a-sil" of Insta-Mold Products, Inc. of Oaks Pa. Note that there are many different types of formable materials (polymers, resins, clay, plastics, etc.) that can be used to create impressions and the foregoing examples are merely exemplary types.

Typically, once the impressions have been made, the housing 106 and formable material 102 are removed from the ear 104 to allow the user to conduct an activity such as wrestling, rugby, etc.; however, if desired, the impressions of formable material 102 and the housing 106 can remain in place during the activity.

Figure 1:
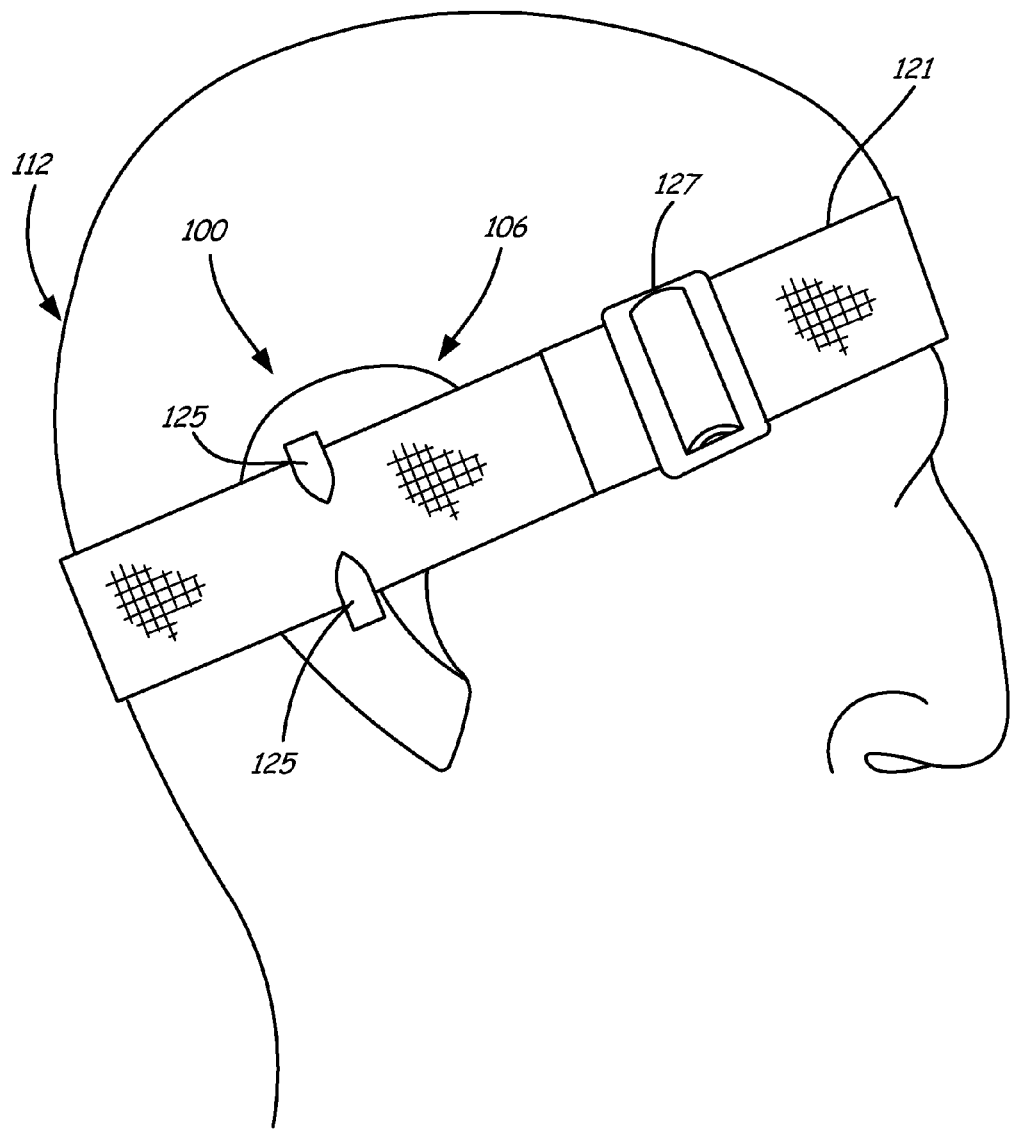
FIG. 1 is a side elevational view of an ear support assembly with a portion of a holding strap.
Figure 4:
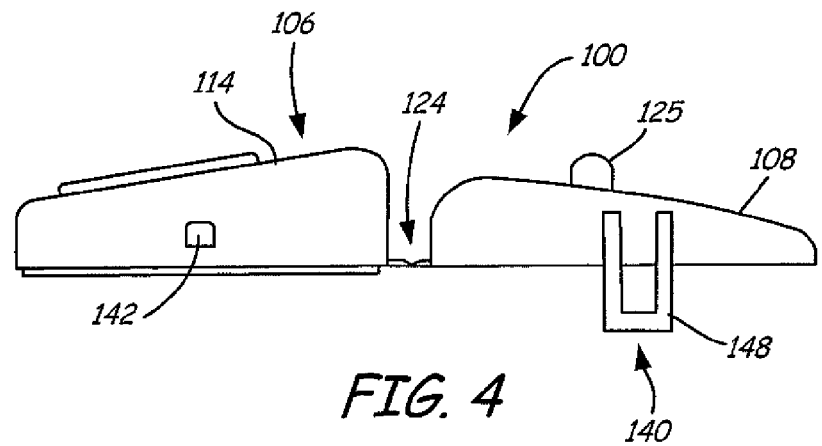
FIG. 4 is a top plan view of the support device for the ear support assembly in the open position.
Figure 5:
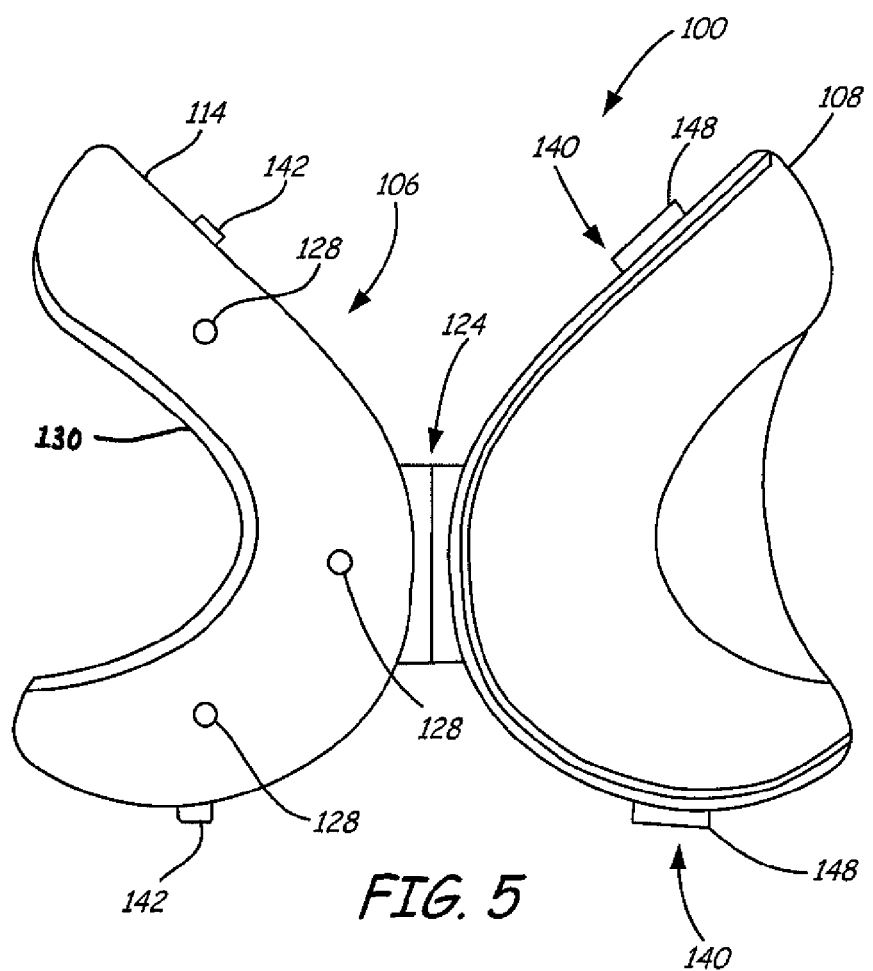
FIG. 5 is an elevational view of inner surfaces of the support device for the ear support assembly in the open position.

If the user has removed the ear support assembly 100 prior to performing the activity and the user suspects that injury has occurred to one or both ears which could result, for example, in a hematoma, one or both of the ear support assemblies 100 are repositioned on each corresponding ear 104 with the impressions of the formable material 102 positioned accordingly on surfaces of the user's ear 104, where the housing 106 retains them in position. Pressure is typically applied through the formable material 102, for example, by locking the portions 108 and 114 of the housing 106 together, in order to reduce swelling and/or reduce the pooling of fluid. Since the ear support assembly 100 comprises a housing 106 enclosing at least a portion of the ear, the ear support assembly 100 is self-supporting on the ear 104, although a restraint such a connecting arm between the ear support assemblies (not shown) or a strap 121 as illustrated in FIG. 1 can be provided, if desired. The restraint can be used to support one or both of the ear support assemblies 100. In the embodiment illustrated, the strap 121 is removably attached to the ear support assemblies 100, wherein the ear support assemblies 100 are held upon the strap 121, for example, with tabs 125. Other fastening mechanisms for holding the ear support assemblies on the restrain such as strap 121 can include hook and loop fasteners, snaps and the like. The strap 121 can be elastic and/or include a fastening mechanism such as a buckle 127 or the like to adjust the length of the strap 121 to the user's head.

In the embodiment illustrated, the housing 106, the first portion 108 and the second portion 114 are in the form of a "C" or crescent (or a backward "C" depending on which ear 104 the housing 106 is designed for). The portions 108 and 114 can be hinged together, as illustrated, or otherwise connectable as separate parts with complimentary mating surfaces. In the embodiment illustrated in FIGS. 1-5, a hinge 124 is provided on surfaces of the portions 108, 114 considered the back of the housing 106, which are proximate the back edge, rim 120 or helix (not shown) of the ear 104. The hinge 124 can be separately affixed to the portions 108, 114 or can be integral therewith where the hinge 124 and the portions 108, 114 are formed as a single unitary body. In this embodiment, whether the portions 108, 114 are hinged or otherwise connectable as separate parts, the housing 106 forms an enclosure that retains the formable material 102 in place so as to deform the formable material 102 and take the impressions of the surfaces of the ear 104 as well as to retain the formable material 102 in place if possible injury has occurred to the ear 102 and it is desired to reduce swelling.

To aid in holding the formable material 102 in place on the housing 106 or portions 108, 114 thereof, attachment structures in the form of projections, recesses and/or apertures can be provided. Referring to the exemplary embodiment illustrated in FIG. 5, the attachment structures include upstanding projections 128 and an enlarged rim on a front edge 130 of the portion 114 positioned proximate a portion of the ear 104 that extends outwardly from the user's skull 112. When the formable material 102 is positioned on the portion 114, the projections 128 tend to be imbedded in the formable material 102 or otherwise surround each of the projections 128 so as to retain the formable material 102 in place. As illustrated in FIG. 8, the formable material 102 can also surround the rim 120 so as to provide additional support on the portion 114. In the embodiment illustrated, portion 108 of the housing 106 does not include any attachment structures although some can be provided, if desired.

In the embodiment illustrated in FIG. 8, the formable material 102 includes two separate portions where a first portion 102A is held and retained by the portion 114 of the housing 106 against the surfaces 116. A second portion 102B conforms to the surfaces 110 of the ear 104 facing away from the user's skull 112 and, in the embodiment illustrated, is inserted separately into the ear 104 and then held in place by the portion 108 of the housing 106. Although use of separate portions of formable material portions 102A and 102B can be easy to work with, the use of separate portions of formable material should not be considered required or limited.

Referring back to FIGS. 2-5, one or more latches 140 are provided to hold the portions 108, 114 of the housing 106 proximate each other. The latches 140 can take many different forms as appreciated by those skilled in the art. In the embodiment illustrated, two latches are provided with a first latch 140 on an upper side of the housing 106 corresponding to an upper portion of the user's ear 104. A second latch 140 is disposed proximate the user's ear lobe on a lower portion of the housing 106. The exemplary latch mechanisms illustrated each include a projection 142 that engages a flexible member 148 having a recess or aperture configured to receive the projection 142.

Figure 6:
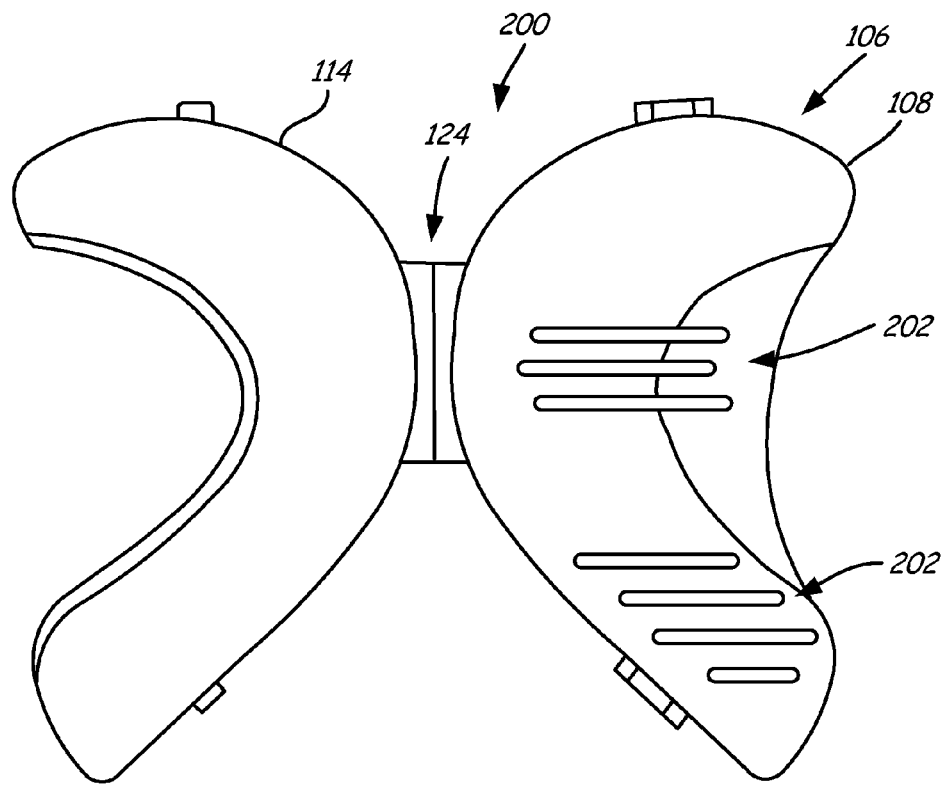
FIG. 6 is an elevational view of outer surfaces of a support device for a second embodiment of an ear support assembly in an open position.
Figure 7:
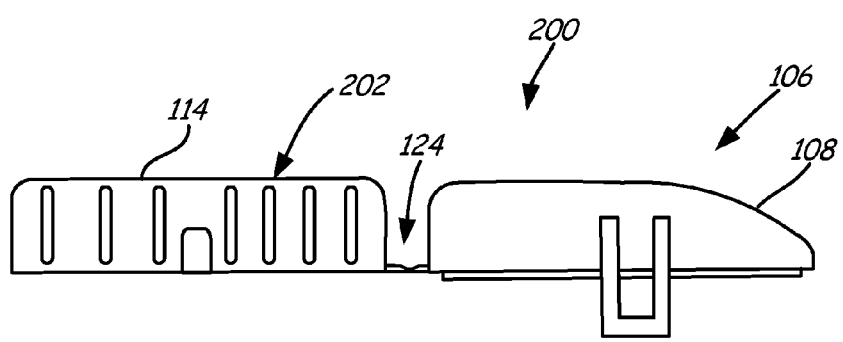
FIG. 7 is a top plan view of the support device for the second embodiment of an ear support assembly in an open position.

FIGS. 6-7 illustrate a second embodiment an ear support assembly 200. The ear support assembly 200 is substantially similar to the ear support assembly 100 described above where similar components have been identified with the same reference numbers. Ear support assembly 200 also includes apertures 202 so as to provide venting which can aid in comfort while the ear support assembly 200 is worn. The apertures 202 can be disposed on the housing 106 as desired. In the embodiment illustrated, apertures 202 are provided on both an outwardly facing surface of the portion 108 as well as on a perimeter surface of the portion 114, but these again are merely exemplary locations.

Figure 9:
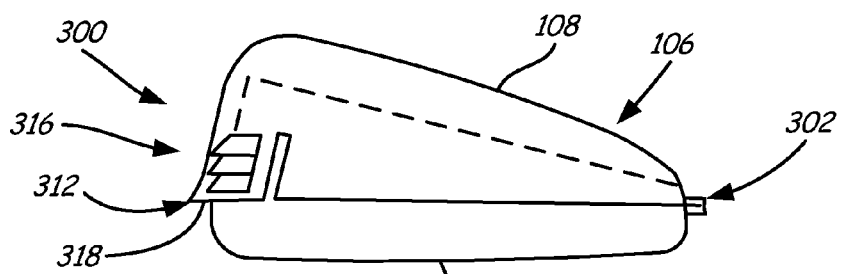
FIG. 9 is a top plan view of a support device for a third embodiment of an ear support assembly in a closed position.
Figure 10:
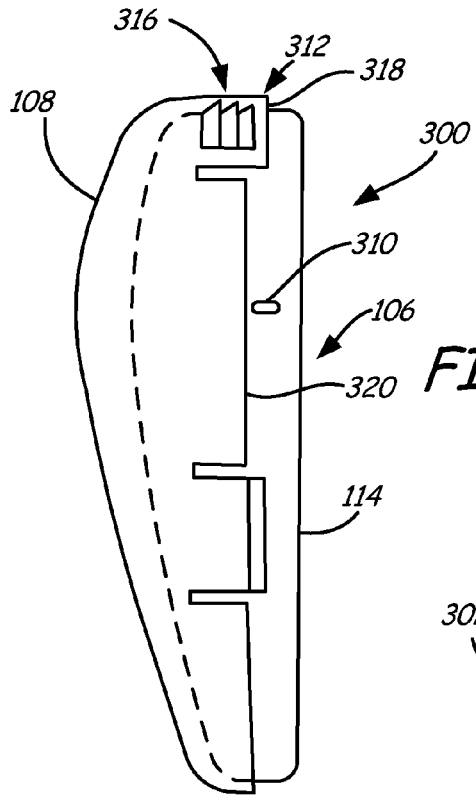
FIG. 10 is a rear elevational view of the support device for third embodiment of the ear support assembly in the closed position.
Figure 11:
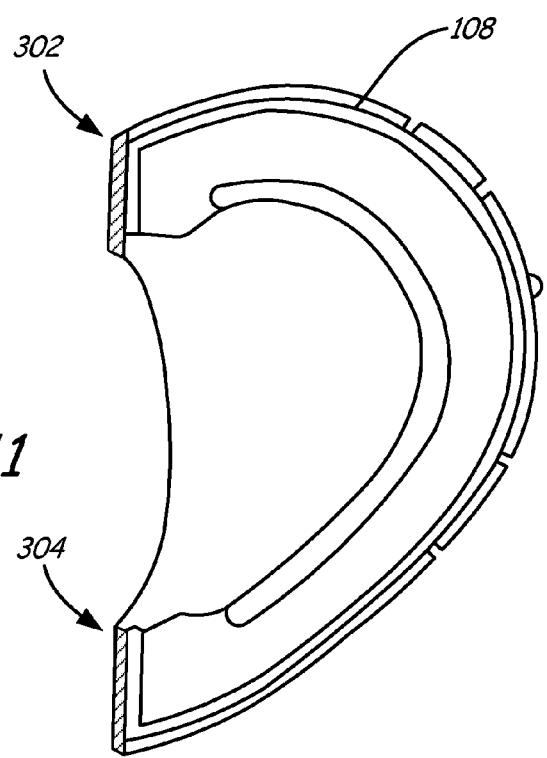
FIG. 11 is a front elevational view of a portion of the third embodiment of the ear support assembly.
Figure 12:
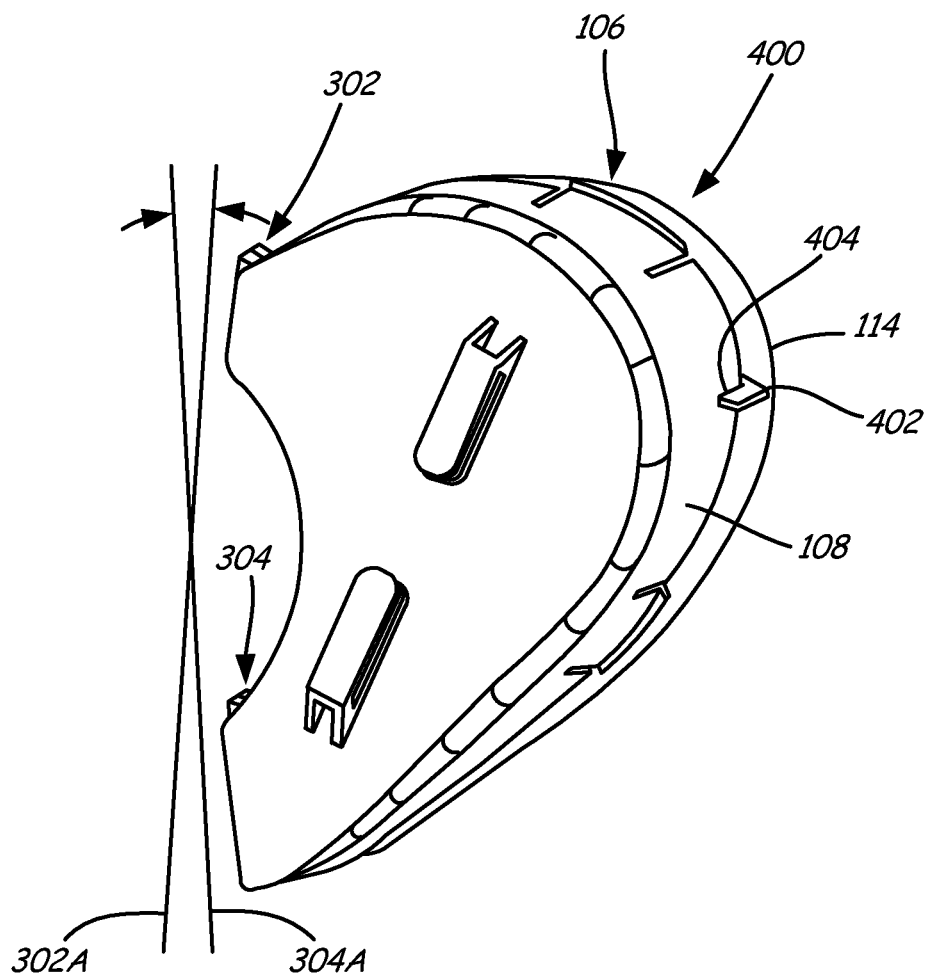
FIG. 12 is a perspective view of a fourth embodiment of an ear support assembly in a closed position.

FIGS. 9-11 illustrate another embodiment of an ear support assembly 300. The ear support assembly 300 is substantially similar to the ear support assembly 100 described above where similar components have been identified with the same reference numbers. The ear support assembly 300 also is a clam shell enclosure having housing 106 with portions 108 and 114; however, in this embodiment, hinges 302 and 304 (portions of which are illustrated in FIG. 11) are provided along a front portion of the housing 106 wherein the first hinge 304 is provided proximate the user's ear lobe and a second hinge 302 is provided also along the front portion of the housing 106 but on an upper portion thereof.

The ear support assembly 300 also illustrates another embodiment of a latch mechanism 312. The latch mechanism 312 allows the portions 108 and 114 of the ear support assembly 300 to be brought together and held at varying distances relative to each other. In a first latch position, the portions 108 and 114 are furthest from each other but still attached to form a clam shell enclosure. This position may be useful when making impressions of the ear with the formable material 102. When possible injury to the ear has occurred, the ear support assembly 300 can be repositioned back on the user's ear 104 where the portions 108, 114 can be brought together and latched in the first position, or alternatively, latched in another position where the portions 108, 114 are brought closer together, thus exerting more pressure upon the surfaces of the ear 104. Although illustrated where the latch mechanism 312 provides three discrete holding positions between the portions 108, 114 (corresponding to the three wedge shaped projections 316 for the flexible member 318), it should be understood that this is but one embodiment and more or less holding positions can be provided in the latch mechanism 312. Likewise, although the latch mechanism 312 herein illustrated provides discrete holding positions, if desired, any suitable latching mechanism allowing for finer adjustments such as through a threaded bolt and nut could be used. As appreciated by those skilled in the art, other forms of latching mechanisms can be employed to hold portions 108 and 114 together in this or any other embodiment herein described. Such mechanisms can include but are not limited to include hook and loop fasteners, snaps, catches or the like.

In an alternate method of use of an ear support assembly such as ear support assembly 300, the impressions made in the formable material 102 can be made when the ear 104 is uninjured and the portions 108, 114 of the housing 106 are closest together. When injury to the ear 104 has occurred and, for example, swelling already exists, the ear support assembly 300 can be reattached to the user's ear 104 and the portions 108, 114 can be held relative to each other at a distance greater then when the impressions were made, (e.g. with the latch mechanism 312 in a position where the portions 108, 114 are furthest apart). Over time as the user wears the ear support assembly 300, the housing portions 108, 114 can be brought closer together and held at selected distances apart from each other for selected intervals of time as desired.

FIGS. 10 and 11 further illustrate a stop 310 that limits the amount of distance between the portions 108, 114, or in other words, how close the portions 108, 114 can be brought together. In this exemplary embodiment, the stop 310 is provided on portion 114 and contacts an edge 320 of portion 108. In use, the stop 310 can be used while the impressions of the ear 104 with the formable material 102 are made by limiting how far apart the portions 108, 114 are relative to each other. Once the impressions are made, the stop 310 can be removed so as to allow the housing portions 108, 114 to be brought closer together (e.g. with operative positions of the latch mechanism 312 adjusted accordingly), if desired, when the ear support assembly 300 is placed back on the ear to inhibit swelling or fluid pooling. Although illustrated where the stop 310 is provided on the portion 114, it should be understood that if desired the stop 310 can also be positioned on the portion 108. Furthermore, it should be understood that the stop 310 can be used on any of the embodiments herein described.

Figure 13:
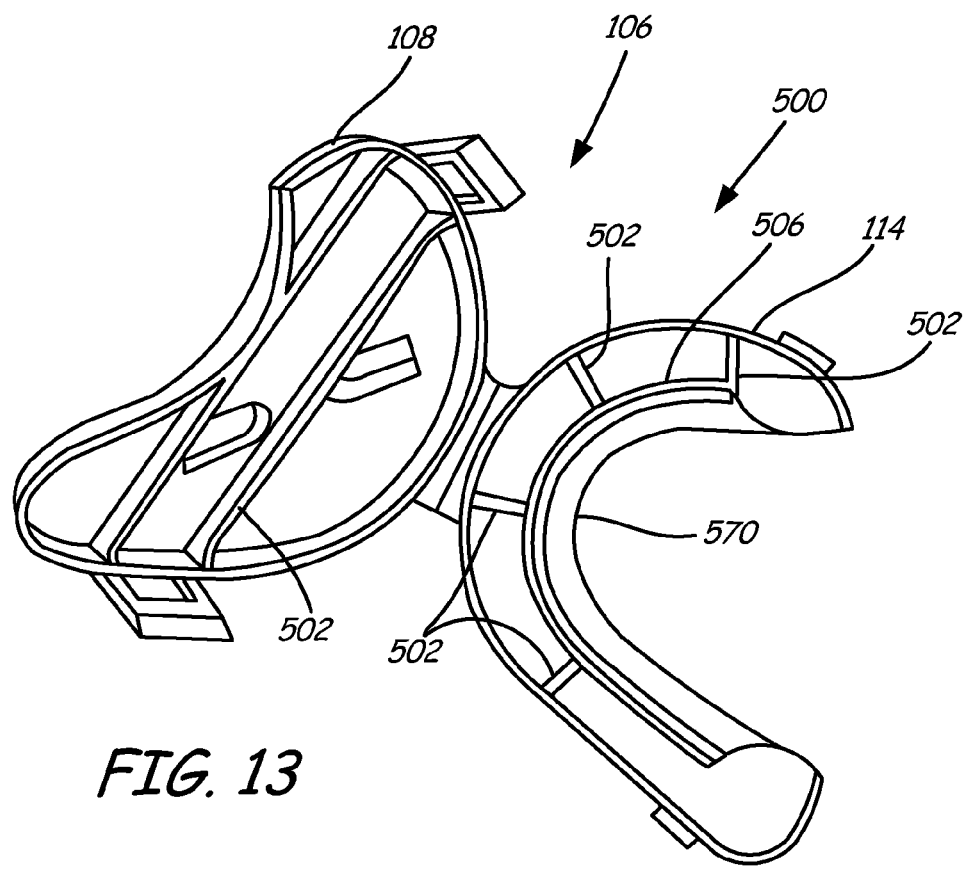
FIG. 13 is a perspective view of a support device for the fourth embodiment of an ear support assembly in an open position.
Figure 14:
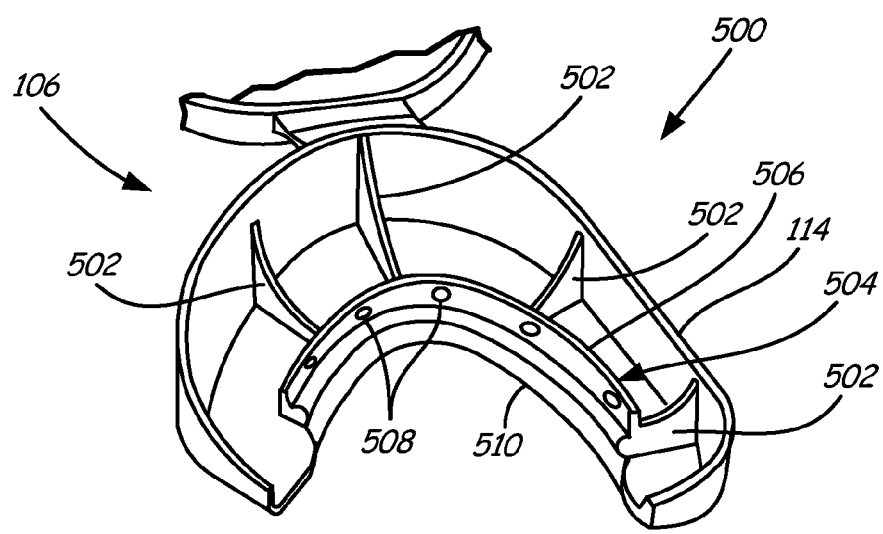
FIG. 14 is another perspective view of a portion of the fourth embodiment of the ear support assembly.

FIGS. 13 and 14 illustrate an ear support assembly 500. The ear support assembly 500 is substantially similar to the ear support assembly 100 described above where similar components have been identified with the same reference numbers. The ear support assembly 500 includes other forms of attachment structures for retaining the formable material 102 on portions 108, 114. In this embodiment, the attachment structures include upstanding ribs 502 and a rim 504 having an upstanding surface 506 and apertures 508 to receive formable material 102 therein. Support assembly 500 further illustrates that portion 114 can include a cushion or pad 510 on a back surface facing the scull 112 (FIG. 2). The cushion or pad can be separately attached or positioned to engage the portion 14, or for example, can be formed on the portion 114 such as through overmolding.

Figure 15:
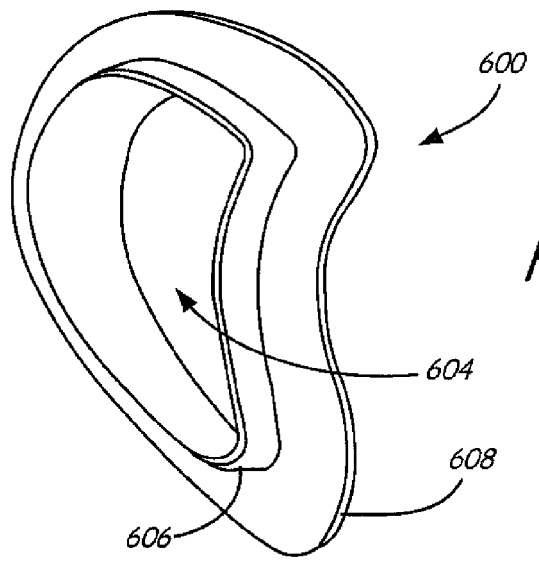
FIG. 15 is a perspective view of an insert for headgear for use with an ear support assembly.
Figure 16:
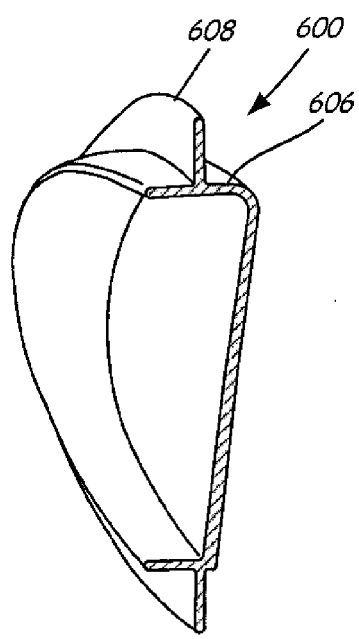
FIG. 16 is a sectional view of the insert.
Figure 17:
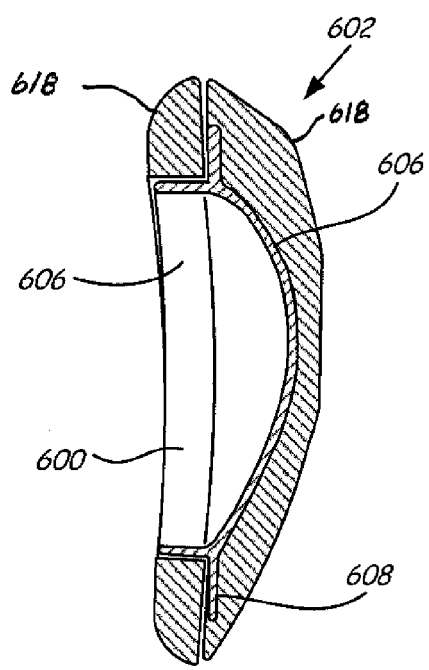
FIG. 17 is a schematic illustration of the insert in headgear.

FIGS. 15-17 illustrate an insert 600 that can be used with headgear often worn by individuals playing sports such as wrestling, boxing or mixed martial arts to name just a few. FIG. 17 illustrates a shell 602 (in cross-section) of the headgear which would be placed over a user's ear. It should be noted that other portions of the headgear such as straps to hold the shells in place are not shown but are well known in the art. The insert 600, which can be made from a flexible material, such as but not limited to rubber or the like, and includes a recess 604 configured for receiving any of the ear support assemblies herein described. Inner surface portions of wall(s) 606 of the recess 604 can engage portion(s) of the ear support assembly, while outer surfaces portions of the wall 606 can be used with or without other portions such as flange 608 to hold the insert 600 in place in the shell 602. If desired, the recess 604 can be configured so as to minimize contact, if any, with the ear support assembly if that is what is preferred. Padding or a cushion material 610 is commonly provided on the shell to contact the user's skull about the ear. As indicated above, if desired, padding or cushion material can also be provided on a surface of the portion 114 of the housing 106 facing the skull to provide additional comfort while the user wears the ear support assembly and headgear.

Figure 18:
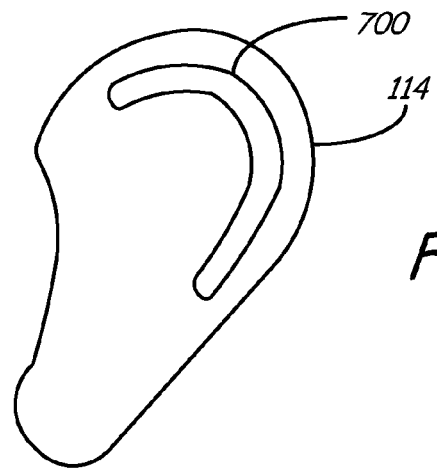
FIG. 18 is a schematic view of an insert for use with the ear support assembly.
Figures 19, 20:
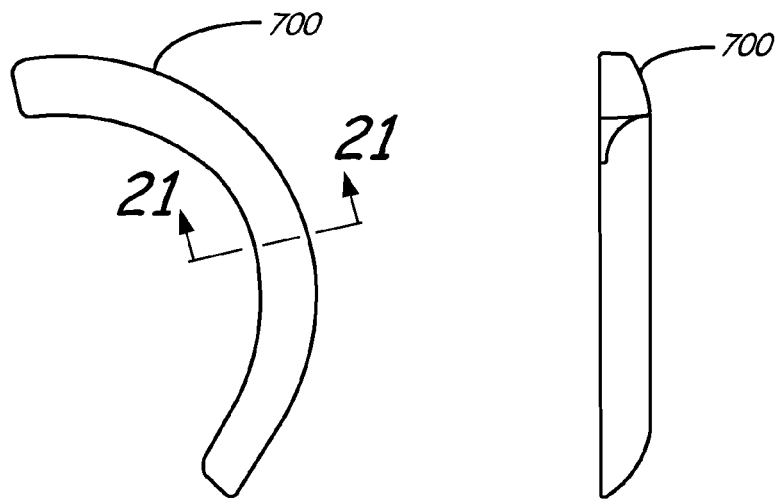
FIG. 19 is an elevational view of the insert of FIG. 18.
FIG. 20 is a side elevational view of the insert of FIG. 18.
Figure 21:
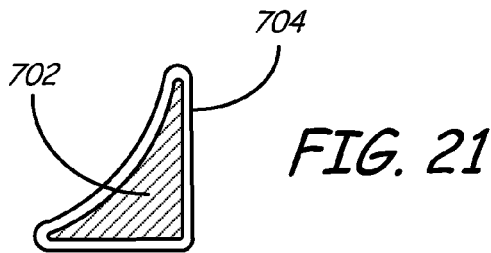
FIG. 21 is a sectional view of the insert taken along lines 21-21 in FIG. 19.
Figure 22:
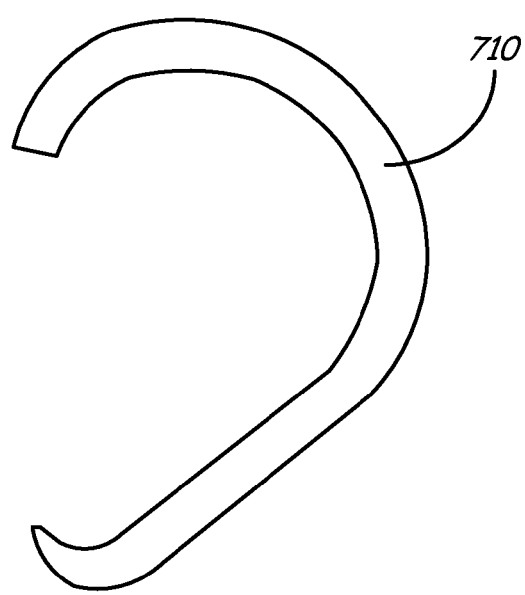
FIG. 22 is an elevational view of a second embodiment of an insert.
Figure 23:
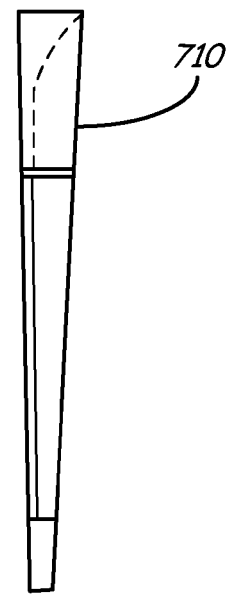
FIG. 23 is a side elevational view of the insert of FIG. 22.

FIGS. 18-25 illustrate optional inserts that can be provided in any of the ear support assemblies herein described. The insert 700 is carried by the support device such as portions 108, 114 of the housing 106. In particular, the insert 700 is attached to or molded with the support device and/or embedded in the formable material. Generally, the insert 700 is filled with or comprises a refrigerant material that can be chilled and/or frozen so that the impression made of the formable material can be kept cool for at least a period of time. FIG. 18 schematically illustrates a crescent-shaped insert 700 that can, for example, be attached to or molded into the portion 114 of the housing 106 such that the insert 700 is embedded into or otherwise is in contact with the impression of the formable material associated with the portion 114. FIGS. 19 and 20 provide front and side elevational views, respectively, of the crescent-shaped insert 700, while FIG. 21 provides a cross-section of the insert 700 showing refrigerant material 702 within a casing 704. FIGS. 22 and 23 illustrates another insert 710 that is similar in construction to that of insert 700 but has a crescent-shape of longer extent—that being substantially similar to the helix of a human ear.

Figure 24:
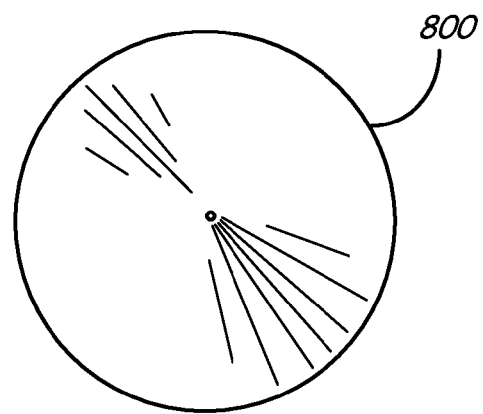
FIG. 24 is a side elevational view of a third embodiment of an insert.
Figure 25:
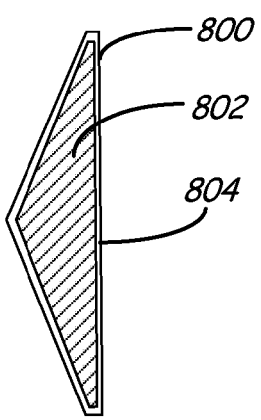
FIG. 25 is a sectional view of the third embodiment of the insert taken along lines 25-25 in FIG. 24.

FIGS. 24 and 25 illustrate a cone-shaped insert 800 that can be carried by a support device associated with formable material used with surfaces 110 of the ear such as portion 108 of housing 106. As with the insert 700 described above, the insert 800 can be attached to or molded with portion 108 and/or embedded into the formable material. FIG. 25 provides a cross-section of the insert 800 showing refrigerant material 802 within a casing 804. It should be noted that the shapes of the foregoing inserts although are advantageous are also merely exemplary and other shapes can be used if desired.

Figure 26:
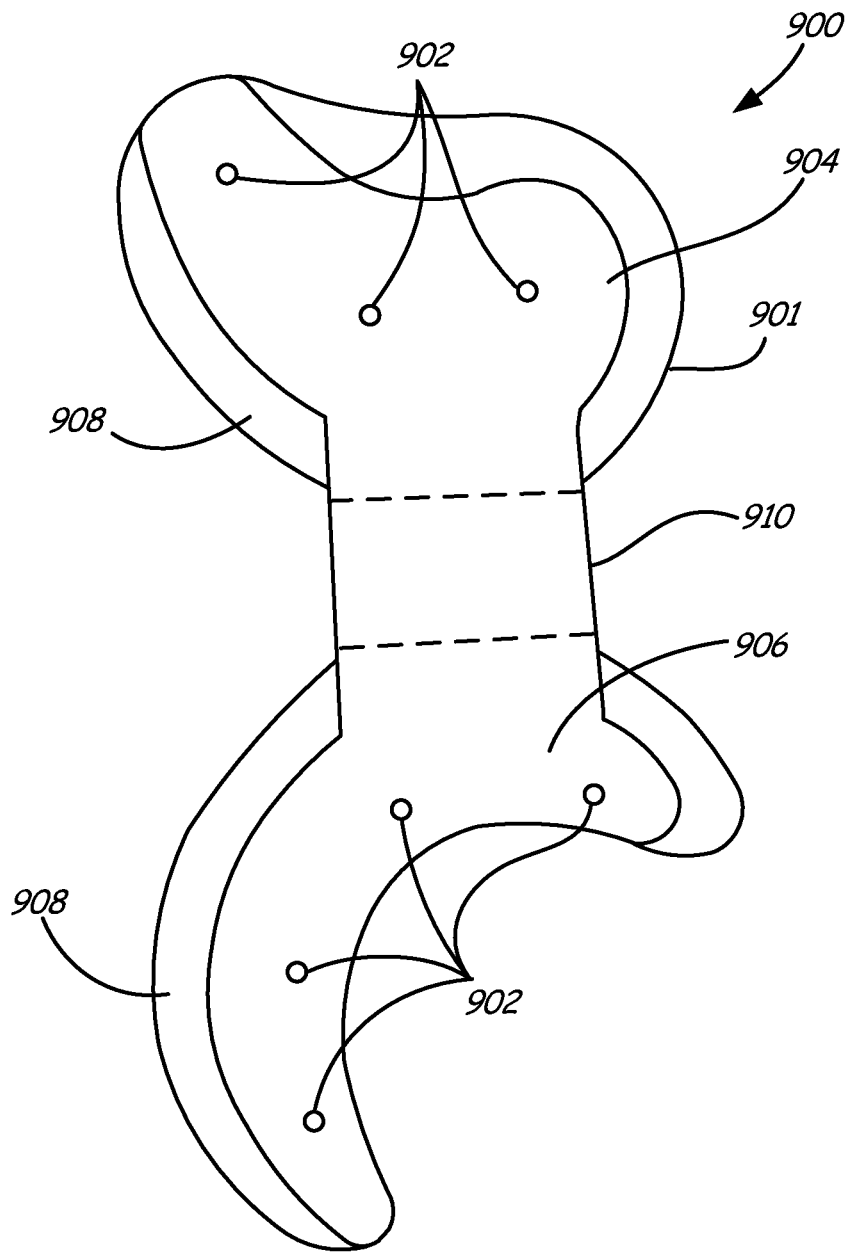
FIG. 26 is a top plan view of a support device for a fifth embodiment of an ear support assembly.

Another support device for holding formable material is illustrated in FIG. 26 at 900. In this embodiment, the ear support 900 includes a support device 901 for the formable material that is generally flat, although this should not be considered necessary or limiting. The formable material (not shown) is attached or otherwise secured to the support device 901 for example using attachment structures comprising projections 902 (as illustrated), recesses or apertures. The support device 901 has a first portion 904 for holding formable material against the surfaces 110 of the ear 104 facing away from the user's skull 112 and a second portion 906 for holding formable material to engage surfaces 116 of the ear 104 facing the user's skull 112. Perimeter portions 908 of each of the portions 904, 906 can include a beveled surface, if desired.

The support device 901 can include a bendable section 910 that can be attached to the first portion 904 and the second portion 906. If desired, the bendable section 910 can be formed integral with portions 904, 906 from a single unitary body. The bendable section 910 allows the portions 904 and 906 to be positioned so that the formable material attached thereto faces each other. In this manner, the formable materials of the portions 904 and 906 can be positioned as in the previous embodiments behind and in front of the ear 104 whereupon when pressure is applied suitable impressions of the surfaces of the ear 104 are obtained. The bendable section 910 also allows the ear support assembly 900 to be removed from the ear when desired and reattached to the ear when necessary. Suitable fasteners such as those described above can be provided to allow the portions to be releasably secured to each other and/or to allow the ear support assembly 900 to be attached to strap or other form of restraint. In this embodiment, the strap or other restraint may be particularly helpful in generating sufficient pressure upon the formable material impressions via the portions 904, 906 in order to reduce swelling and/or pooling of fluid.

Figure 27:
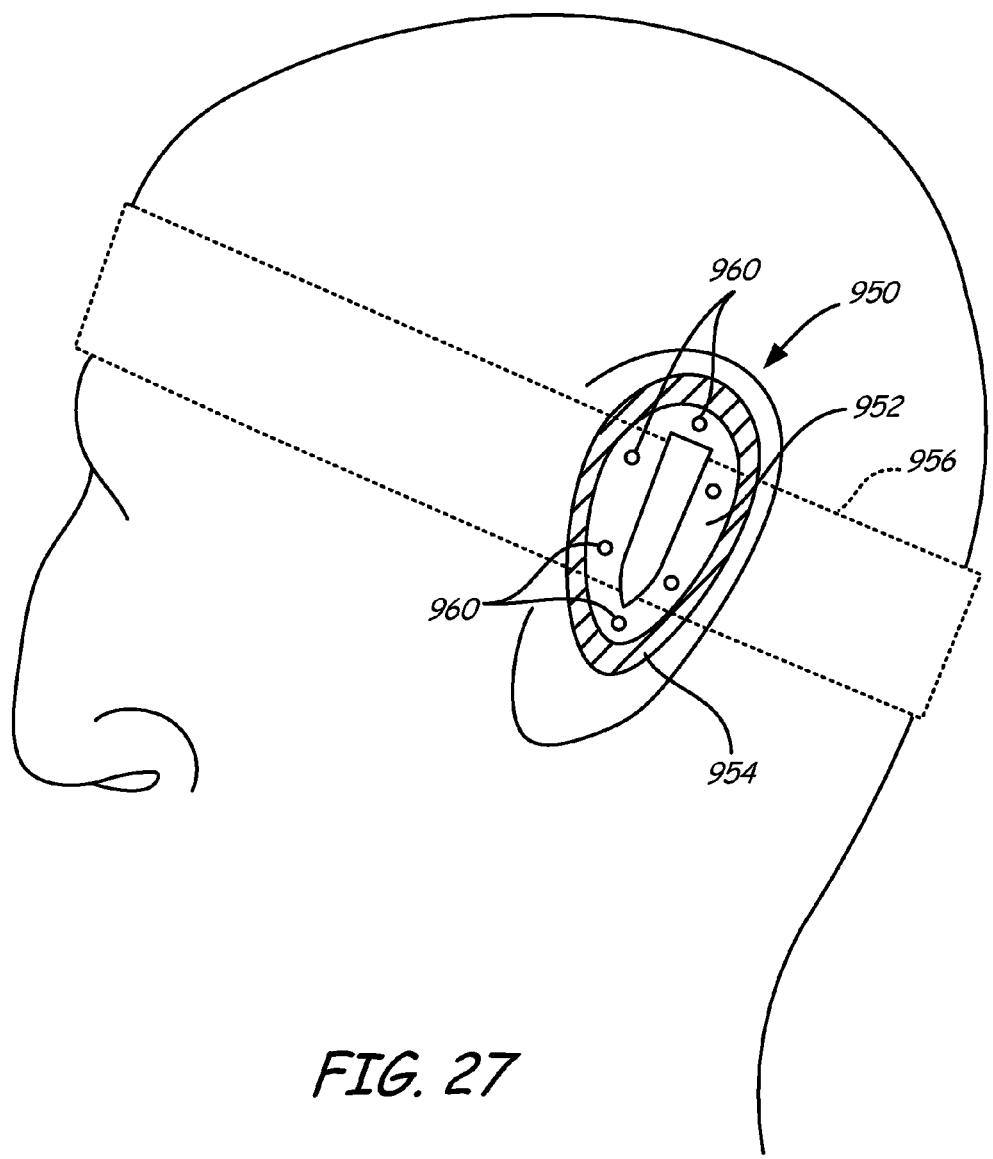
FIG. 27 is an elevational view of a sixth embodiment of an ear support assembly.
Figure 28:
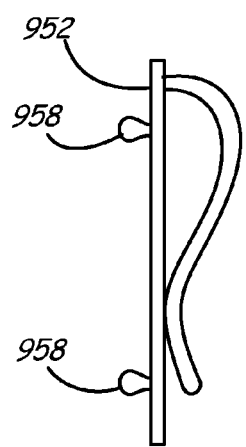
FIG. 28 is an elevational view of a support device for the sixth embodiment of the ear support assembly.

An ear support assembly 950 similar in part to ear support assembly 900 is illustrated in FIGS. 27 and 28. In the embodiment illustrated, ear support assembly 950 includes a single support device 952 for carrying formable material 954 in a manner similar to that described above with portion 906. A strap 956 or other restraint such as flexible arm can be used to hold the ear support assembly 950 or assemblies 950 in position on the ear(s) to make an impression of the ear(s) or to apply pressure with the impression(s) if the ear(s) may have been injured. Various forms of attachment structures can be used to hold the formable material 954 on the support device 952. In the embodiment illustrated, the attachment structures include projections 958 and apertures 960. In yet another embodiment, a support device having formable material for the back surfaces of the ear can be provided. This second support device can be similar to support device 952, and more particularly, similar to portion 906 by itself, and can also be attachable to the strap 956 or other restraint separate and apart from support device 952. With the strap 956 in place and applying pressure to support device 952, the user's ear is pushed toward the user's skull to hold the second support device in position for both obtaining an impression in the formable material and/or applying pressure to reduce swelling and/or pooling of fluid.

Although the subject matter has been described in language directed to specific environments, structural features and/or methodological acts, it is to be understood that the subject matter defined in the appended claims is not limited to the environments, specific features or acts described above as has been held by the courts. Rather, the environments, specific features and acts described above are disclosed as example forms of implementing the claims.

What is claimed is:

1. An ear support assembly comprising:
   a support device comprising a first portion that is crescent shaped and of size to be disposed between an ear and a skull of as user, and a second portion of size to be disposed so as to cover a surface of the ear facing away from the skull of the user, the first portion and the second portion being removably attachable to each other to form a housing of size to dispose a portion the ear of the user therein, the first portion and the second portion having solid planar or curved surfaces; and
   formable material configured to be deformed and retain an impression of a surface of an ear, wherein the planar or curved surfaces are configured to apply pressure to the formable material such that the formable material applies pressure to the surface of the ear.

2. The ear support assembly of claim 1 wherein the housing is of size to cover a rim of the ear of the user, wherein formable material is disposed so as to contact a surface of the ear facing the skull of the user, a surface of the ear facing away from the skull of the user and the rim of the ear, each portion being configured to apply pressure to each of the formable materials such that each of the formable materials applies pressure to the corresponding surface of the ear.

3. The ear support assembly of claim 2 wherein the first portion and the second portion are selectively engagable with each other.

4. The ear support assembly of claim 3 wherein the housing is of size to enclose a portion of the ear from a portion of the rim having a helix to proximate a lobe of the user.

5. The ear support assembly of claim 4 wherein the second portion is crescent shaped so as to conform to the ear.

6. The ear support assembly of claim 4 and further comprising a removable stop so as to limit closure of the portions.

7. The ear support assembly of claim 2 and further comprising a fastener to hold the portions together.

8. The ear support assembly of claim 7 wherein the fastener comprises a latch.

9. The ear support assembly of claim 2 wherein at least one of a hinge or a bendable section joins the first and second portions together.

10. The ear support assembly of claim 2 and further comprising a first and second insert each comprising refrigerant material, wherein the first insert is disposed so as to be in contact with the formable material engaging the surface of the ear facing the skull of the user, and wherein the second insert is disposed so as to be in contact with the formable material engaging the surface of the ear facing away from the skull of the user, each insert engaging a portion of the formable material so as to keep the formable material cool for a period of time.

11. The ear support assembly of claim 1 and further comprising a restraint configured to be worn on the head of the user and apply the pressure to the formable material.

12. The ear support assembly of claim 1 and further comprising an attachment structure for retaining the formable material on the support device.

13. The ear support assembly of claim 1 and further comprising an insert having a recess configured to receive the ear support assembly, the insert being further configured to be disposed in protective headgear.

14. The ear support assembly of claim 1 and further comprising an insert comprising refrigerant material, the insert engaging at least some of the formable material to keep the formable material cool for a period of time.

15. The support assembly of claim 1 wherein the support device includes a venting aperture.

16. A method of applying pressure to a surface of an ear, the method comprising:
providing a support device comprising a first portion that is crescent shaped and of size to be disposed between an ear and a skill of a user, and a second portion of size to be disposed so as to cover a surface of the ear facing away from the skull of the user, the first portion and the second portion being removably attachable to each other to form a housing of size to dispose a portion of the ear of the user therein, the first portion and second portion, having solid planar or curved surfaces;
disposing formable material between inner surfaces of the housing and surfaces of the ear; and
connecting the first portion to the second portion to form the housing and apply pressure through the formable material and thereby to the surface of the ear.

17. The method of claim 16 wherein the housing is of size to cover the rim of the ear of the user and wherein disposing the formable material includes disposing material so as to contact the rim of the ear.

18. The method of claim 17 and further comprising applying a restraint configured to be worn on the head of the user, and wherein applying the pressure comprises the restraint applying pressure to the support device.

19. The method of claim 16 and further comprising providing an insert comprising refrigerant material, wherein the insert engages at least some of the formable material to keep the formable material cool for a period of time.

20. The method of claim 16 wherein connecting comprises fastening the portions together such that the portions are varying distances apart from each other.

* * * * *